(12) United States Patent
James et al.

(10) Patent No.: US 8,998,996 B2
(45) Date of Patent: Apr. 7, 2015

(54) KNEE PROSTHESIS SYSTEM WITH STANDARD AND DISTAL OFFSET JOINT LINE

(71) Applicant: Depuy (Ireland), Cork (IE)

(72) Inventors: Peter J James, Nottingham (GB); Richard E Jones, Dallas, TX (US); Benjamin J Sordelet, Columbia City, IN (US); Timothy G Vendrely, Fort Wayne, IN (US); Stephanie M Wainscott, Warsaw, IN (US)

(73) Assignee: Depuy (Ireland), Cork (IE)

( * ) Notice: Subject to any disclaimer, the term of this patent is extended or adjusted under 35 U.S.C. 154(b) by 0 days.

(21) Appl. No.: 13/832,424

(22) Filed: Mar. 15, 2013

(65) Prior Publication Data

US 2014/0081409 A1    Mar. 20, 2014

Related U.S. Application Data

(60) Provisional application No. 61/703,412, filed on Sep. 20, 2012.

(51) Int. Cl.
*A61F 2/38* (2006.01)
*A61F 2/30* (2006.01)

(52) U.S. Cl.
CPC ........... *A61F 2/3886* (2013.01); *A61F 2/30734* (2013.01); *A61F 2002/30334* (2013.01); *A61F 2002/30344* (2013.01); *A61F 2002/30604* (2013.01); *A61F 2002/30616* (2013.01); *A61F 2002/30738* (2013.01)

(58) Field of Classification Search
CPC ....... A61F 2/384; A61F 2/385; A61F 2/3845; A61F 2/30; A61F 2/3836; A61F 2002/30215
USPC .......... 623/20.14, 20.15, 20.21–20.36, 23.24, 623/20.44
See application file for complete search history.

(56) References Cited

U.S. PATENT DOCUMENTS

| | | | |
|---|---|---|---|
| 3,605,123 | A | 9/1971 | Hahn |
| 3,848,272 | A | 11/1974 | Noiles |
| 3,855,638 | A | 12/1974 | Pilliar |
| 4,219,893 | A | 9/1980 | Noiles |

(Continued)

FOREIGN PATENT DOCUMENTS

| | | |
|---|---|---|
| EP | 457222 A2 | 11/1991 |
| EP | 457222 B1 | 11/1994 |

(Continued)

OTHER PUBLICATIONS

European Search Report From Corresponding EPO Patent Application No. 13185424.2-1654, Dated Nov. 5, 2013 (7 Pages).

(Continued)

*Primary Examiner* — Thomas J Sweet
*Assistant Examiner* — Christie Bahena

(57) ABSTRACT

A modular knee prosthesis system includes a femoral component having a stem and a sleeve. The system is modular, and provides the surgeon with the option of distally offsetting the joint line by controlling the relative axial positions of the stem and the sleeve. Alternative options include providing sleeves with tapered bores of different diameters, providing a shim to be placed between the sleeve and the stem and providing the stems as adapters having different diameters.

7 Claims, 8 Drawing Sheets

(56) References Cited

U.S. PATENT DOCUMENTS

| | | | |
|---|---|---|---|
| 4,301,553 A | 11/1981 | Noiles | |
| 4,536,894 A | 8/1985 | Galante | |
| 4,549,319 A | 10/1985 | Meyer | |
| 4,634,444 A | 1/1987 | Noiles | |
| 4,790,852 A | 12/1988 | Noiles | |
| 4,822,366 A | 4/1989 | Bolesky | |
| 4,846,839 A | 7/1989 | Noiles | |
| 4,854,496 A | 8/1989 | Bugle | |
| 5,061,271 A | 10/1991 | Van Zile | |
| 5,080,685 A | 1/1992 | Bolesky | |
| 5,133,760 A | 7/1992 | Petersen | |
| 5,181,928 A | 1/1993 | Bolesky | |
| 5,182,921 A | 2/1993 | Yan | |
| 5,194,066 A * | 3/1993 | Van Zile | 623/20.15 |
| 5,286,260 A | 2/1994 | Bolesky | |
| 5,290,313 A | 3/1994 | Heldreth | |
| 5,330,534 A | 7/1994 | Herrington | |
| 5,370,706 A | 12/1994 | Bolesky | |
| 5,556,433 A | 9/1996 | Gabriel | |
| 5,593,449 A | 1/1997 | Roberson, Jr. | |
| 5,653,765 A | 8/1997 | McTighe | |
| 5,658,349 A | 8/1997 | Brooks | |
| 5,683,472 A | 11/1997 | O'Neil | |
| 5,782,920 A | 7/1998 | Colleran | |
| 5,782,921 A | 7/1998 | Colleran | |
| 5,824,097 A | 10/1998 | Gabriel | |
| 5,876,459 A | 3/1999 | Powell | |
| 5,879,341 A | 3/1999 | Odorzynski | |
| 5,879,391 A | 3/1999 | Slamin | |
| 5,906,644 A | 5/1999 | Powell | |
| 5,944,756 A | 8/1999 | Fischetti | |
| 5,984,969 A | 11/1999 | Matthews | |
| 6,005,018 A | 12/1999 | Cicierega | |
| 6,053,945 A * | 4/2000 | O'Neil et al. | 623/20.32 |
| 6,071,311 A * | 6/2000 | O'Neil et al. | 623/20.15 |
| 6,126,693 A | 10/2000 | O'Neil | |
| 6,149,687 A | 11/2000 | Gray, Jr. | |
| 6,171,342 B1 | 1/2001 | O'Neil | |
| 6,214,052 B1 | 4/2001 | Burkinshaw | |
| 6,264,699 B1 | 7/2001 | Noiles | |
| 6,428,578 B2 | 8/2002 | White | |
| 6,443,991 B1 | 9/2002 | Running | |
| 6,447,549 B1 * | 9/2002 | Taft | 623/20.15 |
| 6,527,807 B1 | 3/2003 | O'Neil | |
| 6,613,092 B1 | 9/2003 | Kana | |
| 6,723,129 B2 | 4/2004 | Dwyer | |
| 6,727,723 B2 | 4/2004 | Shimizu | |
| 6,824,566 B2 | 11/2004 | Kana | |
| 6,875,239 B2 | 4/2005 | Gerbec | |
| 6,902,583 B2 | 6/2005 | Gerbec | |
| 6,953,479 B2 | 10/2005 | Carson | |
| 7,291,174 B2 | 11/2007 | German | |
| 7,628,818 B2 | 12/2009 | Hazebrouck | |
| 7,799,085 B2 * | 9/2010 | Goodfried et al. | 623/20.15 |
| 8,128,703 B2 | 3/2012 | Hazebrouck | |
| 8,382,849 B2 | 2/2013 | Thomas | |
| 8,424,183 B2 | 4/2013 | Thomas | |
| 8,562,616 B2 | 10/2013 | May | |
| 2002/0133234 A1 | 9/2002 | Sotereanos | |
| 2003/0014120 A1 | 1/2003 | Carson | |
| 2003/0204267 A1 | 10/2003 | Hazebrouck | |
| 2003/0204268 A1 * | 10/2003 | Gerbec et al. | 623/23.44 |
| 2004/0049285 A1 | 3/2004 | Haas | |
| 2004/0172139 A1 | 9/2004 | Dwyer | |
| 2005/0107883 A1 | 5/2005 | Goodfried | |
| 2005/0154470 A1 * | 7/2005 | Sekel | 623/20.15 |
| 2006/0030945 A1 * | 2/2006 | Wright | 623/20.15 |
| 2006/0142867 A1 | 6/2006 | Metzger | |
| 2008/0234830 A1 * | 9/2008 | Hershberger et al. | 623/22.15 |
| 2009/0088862 A1 | 4/2009 | Thomas | |
| 2010/0076565 A1 | 3/2010 | Thomas | |
| 2010/0114323 A1 * | 5/2010 | Deruntz et al. | 623/20.21 |
| 2012/0016482 A1 | 1/2012 | Mooradian | |
| 2013/0085577 A1 * | 4/2013 | Link et al. | 623/23.39 |
| 2014/0081408 A1 | 3/2014 | Lieberman | |
| 2014/0081410 A1 | 3/2014 | Lieberman | |

FOREIGN PATENT DOCUMENTS

| | | |
|---|---|---|
| EP | 947181 A2 | 10/1999 |
| EP | 947181 A3 | 6/2002 |
| EP | 1623686 A2 | 2/2006 |
| EP | 1623686 A3 | 3/2011 |
| FR | 2733411 A1 | 10/1996 |
| WO | WO 9118563 A1 | 12/1991 |
| WO | WO 03065939 A1 | 8/2003 |
| WO | WO 2007053905 A1 | 5/2007 |

OTHER PUBLICATIONS

Biomet, Orthopaedic Salvage System Overview, Available at Least as Early as Aug. 15, 2005, (153 Pages).

Depuy, Reconstructive/Revision Products, 0608-46-000, 2000 (pp. 182 and 184).

Depuy Orthopaedics, Inc., P.F.C. Sigma Knee System With Rotating Platform Technical Monograph, 3M0800, 0611-29-050, 1999, Depuy Orthopaedics, Inc., 700 Orthopaedic Drive, Warsaw, IN 46580, USA.

Depuy Orthopaedics, Inc., LCS Compelte Mobile-Bearing Knee System, 2001, Depuy Orthopaedics, Inc., 700 Orthopaedic Drive, Warsaw, IN 46580, USA.

S-ROM Noiles Rotating Hinge Surgical Technique & Reference Guide, 0601-98-050 (Rev. 2), Depuy Orthopaedics, Inc., 2002, 44 Pages.

EPO Search Report, EPO App. No. 13185435.8-1654, Dec. 11, 2013, 7 Pages.

EPO Search Report, EPO App. No. 13185436.6-1654, Dec. 12, 2013, 8 Pages.

Partial EPO Search Report, EPO App. No. 13185432.5-1654, Jan. 2, 2014, 7 Pages.

* cited by examiner

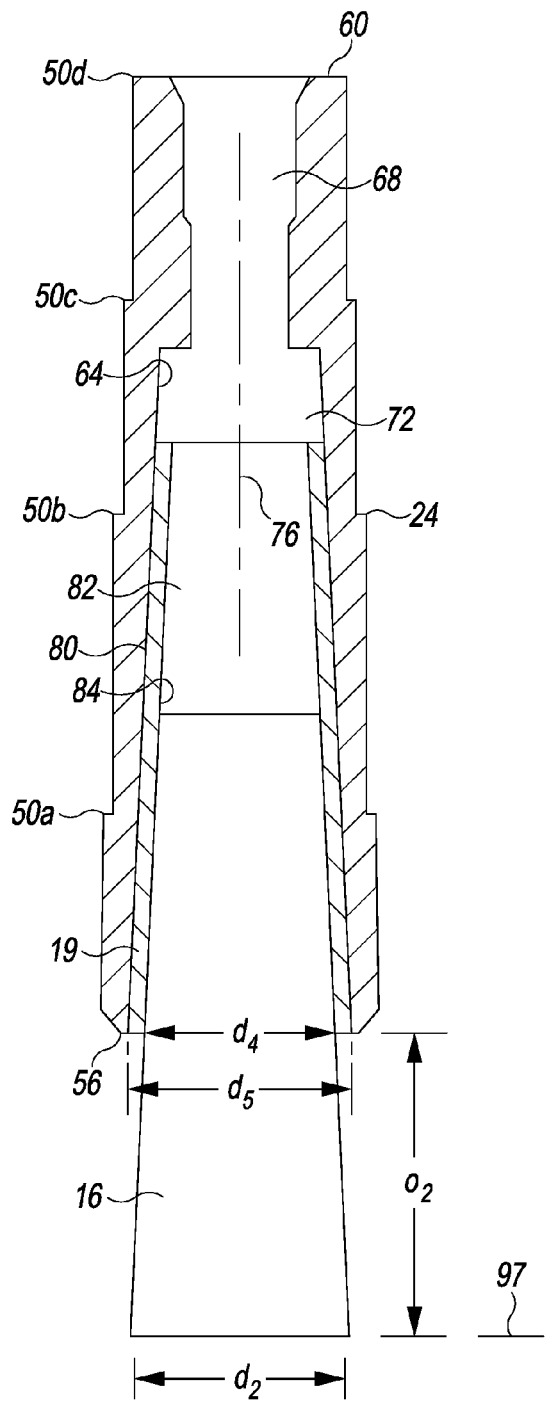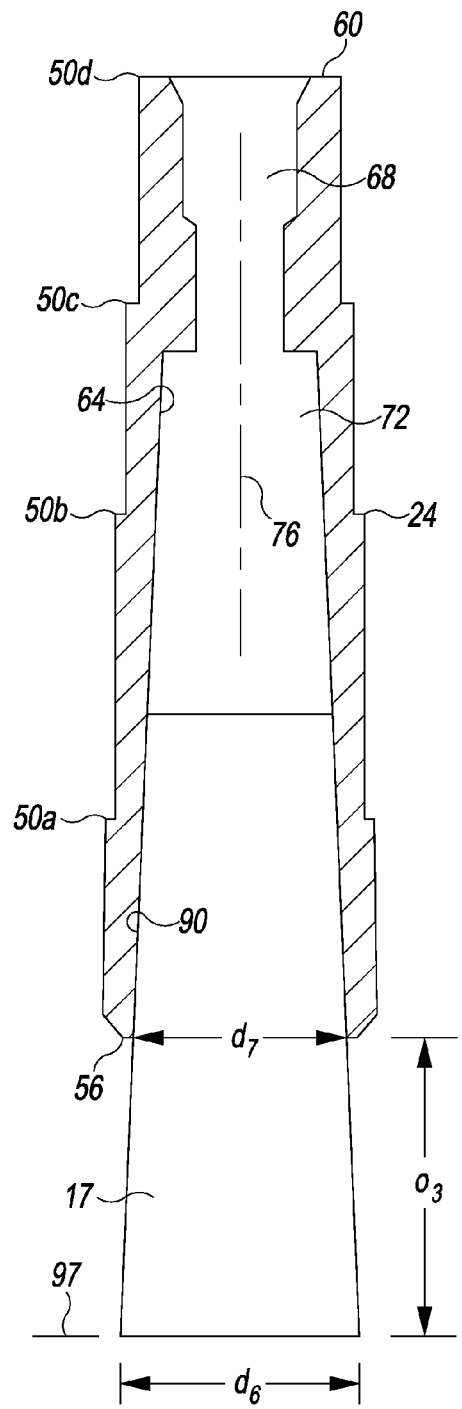
Fig. 7
Fig. 8

KNEE PROSTHESIS SYSTEM WITH STANDARD AND DISTAL OFFSET JOINT LINE

CROSS-REFERENCE TO RELATED APPLICATION

This application claims priority to U.S. Prov. App. No. 61/703,412 filed Sep. 20, 2012, entitled "Knee Prosthesis System with Standard and Distally Offset Joint Line," which is incorporated by reference herein in its entirety.

TECHNICAL FIELD

The present disclosure relates generally to prosthetic joints, and more particularly to a modular prosthetic knee joint system that includes a metaphyseal sleeve component.

BACKGROUND

The knee joint basically consists of the bone interface of the distal end of the femur and the proximal end of the tibia. Appearing to cover or at least partially protect this interface is the patella, which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

When the knee joint is damaged whether as a result of an accident or illness, a prosthetic replacement of the damaged joint may be necessary to relieve pain and to restore normal use to the joint. Typically the entire knee joint is replaced by means of a surgical procedure that involves removal of the surfaces of the corresponding damaged bones and replacement of these surfaces with prosthetic implants. This replacement of a native joint with a prosthetic joint is referred to as a primary total-knee arthroplasty.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

Knee implant systems for both primary and revision applications are available from a variety of manufacturers, including DePuy Synthes Products, LLC. DePuy Synthes and others offer several different systems for both primary and revision applications. For example, DePuy Synthes offers the P.F.C. SIGMA® Knee System, the LCS® Total Knee System, and the S-ROM Modular Total Knee System. These orthopaedic knee systems includes several components, some appropriate for use in primary knee arthroplasty and some appropriate for use in revision surgery.

DePuy Synthes also offers other orthopaedic implant systems for other applications. One such system is the LPS System. The LPS System is provided for use in cases of severe trauma and disease. In such cases, the trauma or disease can lead to significant amounts of bone loss. The LPS System provides components that can replace all or significant portions of a particular bone, such as the femur. The DePuy Synthes LPS System is described more fully in U.S. patent application Ser. No. 10/135,791, entitled "Modular Limb Preservation System", filed Apr. 30, 2002 by Hazebrouck et al. (U.S. Pat. Pub. No. 2003-0204267), which is incorporated by reference herein in its entirety.

In some patients, the metaphysis of the bone near the joint presents cavitary defects that are not completely filled by standard knee implants. The presence of such metaphyseal defects can result in loosening of the prosthetic implant over time, compromising the stability of the prosthetic implant and frequently requiring revision of the prosthetic implant.

To fill metaphyseal cavitary defects, knee systems with modular metaphyseal sleeves have been provided. Such sleeves are illustrated, for example, in: U.S. Pat. Pub. No. 2010/0114323, entitled "Knee Prosthesis Kit with Winged Sleeves and Milling Guide;" U.S. Pat. Pub. No. 2006/0030945A1, entitled "Modular Orthopaedic Implant System With Multi-Use Stems;" U.S. Pat. No. 7,799,085, entitled "Modular Implant System With Fully Porous Coated Sleeve;" U.S. Pat. No. 7,291,174, entitled "Prosthetic Tibial Component With Modular Sleeve;" U.S. Pat. No. 6,171,342, entitled "Medical Fastening System;" U.S. Pat. No. 5,824,097, entitled "Medical Fastening System;" U.S. Pat. No. 5,782,921, entitled "Modular Knee Prosthesis;" and U.S. Pat. No. 4,634,444, entitled "Semi-Constrained Artificial Joint." Such sleeves have been used in commercially available prosthetic knee implant systems, such as the P.F.C. SIGMA.® Knee System, the LCS® Total Knee System, the S-ROM Modular Total Knee System and the LPS System, all available from DePuy Synthes Sales, Inc.

Modular sleeves have also been used in hip implant systems, as illustrated, for example, in: U.S. Pat. No. 6,264,699, entitled "Modular Stem and Sleeve Prosthesis;" and U.S. Pat. No. 4,790,852, entitled "Sleeves for Affixing Artificial Joints to Bone." Such hip sleeves have been used in commercially available prosthetic hip implant systems, such as the S-ROM hip systems, available from DePuy Synthes Sales, Inc. of Warsaw, Ind.

The disclosures of all of the above patent applications and patents are incorporated by reference herein in their entireties.

In knee systems with modular metaphyseal sleeves, the conventional shape of many of the sleeves is generally an elliptical cone with a large ellipse profile close to the joint line tapering down to a smaller elliptical or circular profile at the termination of the component distal to the joint line. Generally, the sleeves have a terraced or stepped outer surface and an inner channel for frictional fixation to another component. This geometry fills cavitary defects in the metaphysis, allows for a wider surface area for load transfer through the joint and provides rotational stability for the articulating components of the prosthesis.

The outer surface of the sleeve is supported by solid bony structure or the bone bed. In the case of the distal femur, patient anatomy and the condition of the bone, particularly in a revision surgery, may require that the distal femur be resected to a more proximal level. Implanting a prosthetic distal femoral component and sleeve at this more proximal level may elevate the joint line (that is, the line defined by the articulation of the articular surfaces of the distal femoral component and proximal tibial component). Elevation of the joint line may adversely affect performance of the prosthetic knee system: the positions of the collateral ligament attachments to the femur relative to the joint line may impact knee kinematics, the articulation of the patella against the femoral component will be impacted, and the function of the extensor mechanism will also be impacted.

Prosthetic knee implant systems have commonly included femoral augments for use on the distal and posterior bone-facing surfaces of the femoral implant components. Examples of such augments are disclosed in U.S. Pat. Nos. 6,005,018 and 5,984,969, which are incorporated by reference herein in their entireties. Such components serve to augment the inferior and posterior portions of the femoral component to add additional thickness to compensate for the lack of sufficient boney tissue, allowing the joint line to be distalized. However, with the femoral component so distalized, the metaphyseal sleeve used with the femoral component may no longer be optimally seated on a healthy bone bed. To compensate, surgeons may sometimes opt to use a larger size of metaphyseal sleeve.

Accordingly, a need exists for a knee prosthesis system that allows the surgeon the flexibility to optimize the position of the joint line while also allowing for a metaphyseal sleeve to be optimally sized and optimally positioned on a healthy bone bed.

SUMMARY

The present invention provides a modular knee implant system that allows the surgeon to use an optimally sized metaphyseal sleeve with a distal femoral component while also allowing for optimization of the joint line.

According to one aspect of the present disclosure, a modular knee prosthesis system is provided. The system includes a distal femoral component, a first metaphyseal member and a second metaphyseal member. The distal femoral component has a pair of spaced, curved distal condylar surfaces and a stem having an outer surface tapering from a distal end in the proximal direction. The outer surface of the stem has a maximum outer diameter at the distal end and a smaller outer diameter at a second position proximal to the distal end. The metaphyseal member has an outer surface that tapers in a proximal direction and an inner surface defining a tapered bore sized and shaped to be mountable on the stem of the distal femoral component and to create a frictional lock between the stem of the distal femoral component and the first metaphyseal member. The tapered bore has a maximum inner diameter at a distal end; the maximum inner diameter corresponds with the maximum outer diameter of the stem of the distal femoral component. The second metaphyseal member also has an outer surface that tapers in a proximal direction and an inner surface defining a tapered bore sized and shaped to be mountable on the stem of the distal femoral component and to create a frictional lock between the stem of the distal femoral component and the second metaphyseal member. The tapered bore has a maximum inner diameter at a distal end; the maximum inner diameter corresponds with the outer diameter of the stem of the distal femoral component at the second position so that the first metaphyseal member and the second metaphyseal member are mountable on the stem of the distal femoral component to create frictional locks at different positions in the proximal-distal direction on the stem of the distal femoral component.

In an illustrative embodiment, the second metaphyseal member comprises an assembly of a sleeve and a first shim. The sleeve has an outer surface that defines the outer surface of the second metaphyseal member and an inner surface defining a tapered bore sized and shaped to be mountable on the stem of the distal femoral component and to create a frictional lock between the stem of the distal femoral component and the sleeve. The tapered bore has a maximum inner diameter at a distal end and a smaller inner diameter at a second more proximal position. The size and shape of the tapered bore of the sleeve are substantially the same as the size and shape of the tapered bore of the first metaphyseal member. The first shim comprises a tapered tube having an outer surface sized and shaped to be received within and frictionally lock with the tapered bore of the sleeve and an inner surface defining a tapered bore sized and shaped to be mountable on the stem of the distal femoral component and to create a frictional lock between the stem of the distal femoral component and the first shim. The tapered bore of the first shim has a maximum inner diameter at a distal end and a second inner diameter at a second more proximal position. The maximum inner diameter of the first shim defines the maximum inner diameter of the second metaphyseal member when the first shim and sleeve are assembled.

In a more particular embodiment, a distal portion of the stem is exposed when the sleeve and first shim are frictionally locked on the stem.

In another more particular embodiment, the outer surfaces of the first metaphyseal member and the sleeve have the same size and shape.

In another more particular embodiment, the stem has a distal end and the tapered bores of the first and second metaphyseal members have central longitudinal axes. In this embodiment, the central longitudinal axis of each tapered bore intersects a plane at the distal end of the stem of the distal femoral component when the respective metaphyseal member is mounted on the stem of the distal femoral component. With the first metaphyseal member, the distal end of the tapered bore and the plane are spaced a first distance. With the second metaphyseal member, the distal end of the tapered bore and the plane are spaced at a second distance. The second distance is greater than the first distance and the difference between the first distance and the second distance defines a distal offset of the distal femoral component.

In another more particular embodiment, the distal femoral component has a distal bone-facing surface and the system further comprises a distal femoral augment having a thickness. The thickness of the distal femoral augment is substantially the same as the distal offset provided by the second metaphyseal member.

In another more particular embodiment, the system also includes a tibial member having an articulating surface to receive and articulate with the distal articulating surfaces of the distal femoral component. In this embodiment, the contact between the articulating surfaces of the tibial member and the distal femoral component define a joint line. In this embodiment, the tibial member and an assembly of the distal femoral component and the first metaphyseal member defines a first joint line and the tibial member and an assembly of the distal femoral component and the second metaphyseal member defines a second joint line; the second joint line is more distal than the first joint line.

According to another aspect of the present invention, a modular knee prosthesis system comprises a distal femoral component, a first metaphyseal member and two stem adapters. The distal femoral component has a pair of spaced, curved distal condylar surfaces. The first metaphyseal member has an outer surface that tapers in a proximal direction and an inner surface defining a bore tapering from a maximum inner diameter at a distal end to a smaller inner diameter at a second more proximal position. The first stem adapter is selectively mountable on the distal femoral component and has an outer surface tapering from a distal end in the proximal direction; the outer surface of the stem has a maximum outer diameter at a distal end and a smaller outer diameter at a second position proximal to the distal end. The second stem adapter is also selectively mountable on the distal femoral component and has an outer surface tapering from a distal end in the proximal direction; the outer surface of the second stem has a maximum outer diameter at a distal end and a smaller outer diameter at a second position proximal to the distal end. In this embodiment, the maximum outer diameter of the second stem adapter is greater than the maximum outer diameter of the first stem adapter. The bore of the first metaphyseal member is sized and shaped to be mountable on the first stem adapter and to create a frictional lock between the first metaphyseal member and the first stem adapter and to be mountable on the second stem adapter and to create a frictional lock between the first metaphyseal member and the second stem adapter. When the first metaphyseal member and first stem adapter are locked together the distal end of the first stem adapter is in a proximal-distal position with respect to the bore of the first metaphyseal member. When the first metaphyseal member and second stem adapter are locked together the distal end of the second stem adapter is in another proximal-distal position with respect to the bore of the first metaphyseal member. The locked proximal-distal position of the first stem adapter is more proximal than the locked proximal-distal position of the second stem adapter with respect to the first metaphyseal member.

When the first stem adapter is mounted on the distal femoral component and the first metaphyseal member is locked on the first stem adapter the distal femoral component is in a first proximal-distal position with respect to the bore of the first metaphyseal member. When the second stem adapter is mounted on the distal femoral component and the first metaphyseal member is locked on the second stem adapter the distal femoral component is in a second proximal-distal position with respect to the bore of the first metaphyseal member. The second proximal-distal position of the distal femoral component is more distal than the first proximal-distal position of the distal femoral component.

In a more particular embodiment, the difference between the first proximal-distal position of the distal femoral component and the second proximal-distal position of the distal femoral component corresponds with a distal offset of the distal femoral component. The distal femoral component has a distal bone-facing surface and the system may further comprise a distal femoral augment having a thickness. In this embodiment, the thickness of the distal femoral augment may be substantially the same as the distal offset of the distal femoral component.

According to another aspect of the present disclosure, a knee prosthesis system includes a distal femoral component, a shim and a metaphyseal sleeve. The distal femoral component has a pair of spaced, curved distal condylar surfaces and a stem having an outer surface tapering from a distal end in the proximal direction. The outer surface of the stem has a maximum outer diameter at the distal end and a smaller outer diameter at a second position proximal to the distal end. The shim comprises a tapered tube having an outer surface and an inner surface, the inner surface of the shim frictionally locked to the outer surface of the stem. The metaphyseal sleeve has an outer surface that tapers in a proximal direction and an inner surface defining a tapered bore. The inner surface is frictionally locked to the outer surface of the shim and the distal end of the sleeve is spaced from the distal end of the stem.

In another aspect, the present invention provides a modular knee prosthesis system comprising a distal femoral component and first and second metaphyseal members. The distal femoral component has a pair of spaced, curved distal condylar surfaces and a stem. The stem has an outer surface that tapers from a distal end in the proximal direction. The outer surface of the stem has a maximum outer diameter at the distal end and a smaller outer diameter at a second position proximal to the distal end. The first and second metaphyseal members have outer surfaces that taper in a proximal direction from distal ends to proximal ends and inner surfaces defining tapered bores. The tapered bores are sized and shaped to be mountable on the stem of the distal femoral component and to create a frictional lock between the stem of the distal femoral component and the metaphyseal members. The tapered bores extends proximally from openings at the distal ends of the metaphyseal members. The outer surfaces of the first and second metaphyseal members have the same maximum transverse dimensions. When the metaphyseal members are mounted on the distal femoral component with the metaphyseal members frictionally locked to the distal femoral component, each assembly has a maximum axial length. The maximum axial length of the assembly of the second metaphyseal member and the distal femoral component is greater than the maximum axial length of the assembly of the first metaphyseal member and the distal femoral component.

In an illustrative embodiment, the first metaphyseal member and second metaphyseal members have different axial lengths.

In another illustrative embodiment, the first metaphyseal member and second metaphyseal members have the same axial lengths and the opening into the bore of the first metaphyseal member is larger than the opening into the bore of the second metaphyseal member.

In a more particular embodiment, the second metaphyseal member comprises an assembly of a sleeve and a first shim. In this embodiment, the sleeve has an outer surface that defines the outer surface of the second metaphyseal member and an inner surface that defines a tapered bore sized and shaped to be mountable on the stem of the distal femoral component and to create a frictional lock between the stem of the distal femoral component and the sleeve. The tapered bore has a maximum inner diameter at a distal end and a smaller inner diameter at a second more proximal position. The size and shape of the tapered bore of the sleeve is substantially the same as the size and shape of the tapered bore of the first metaphyseal member. The first shim comprises a tapered tube having an outer surface sized and shaped to be received within and frictionally lock with the tapered bore of the sleeve and an inner surface defining a tapered bore sized and shaped to be mountable on the stem of the distal femoral component and to create a frictional lock between the stem of the distal femoral component and the first shim. The tapered bore of the first shim has a maximum inner diameter at a distal end and a second inner diameter at a second more proximal position. The maximum inner diameter of the first shim defines the maximum inner diameter of the second metaphyseal member when the first shim and sleeve are assembled. In this embodiment, a distal portion of the stem may be exposed when the sleeve and first shim are frictionally locked on the stem. Moreover, in this embodiment the outer surfaces of the first metaphyseal member and the sleeve may have the same size and shape.

BRIEF DESCRIPTION OF THE DRAWINGS

The detailed description particularly refers to the accompanying figures in which:

FIG. 7 is a cross-sectional view of the shim and metaphyseal sleeve of the modular knee prosthesis system of FIG. 2, shown mounted on the stem of FIG. 2 (the stem shown in side view);

FIG. 8 a cross-sectional view of the metaphyseal sleeve of the modular knee prosthesis system of FIG. 3, shown mounted on the thicker stem of FIG. 3 (the stem shown in side view);

DETAILED DESCRIPTION OF THE DRAWINGS

Figure 1:
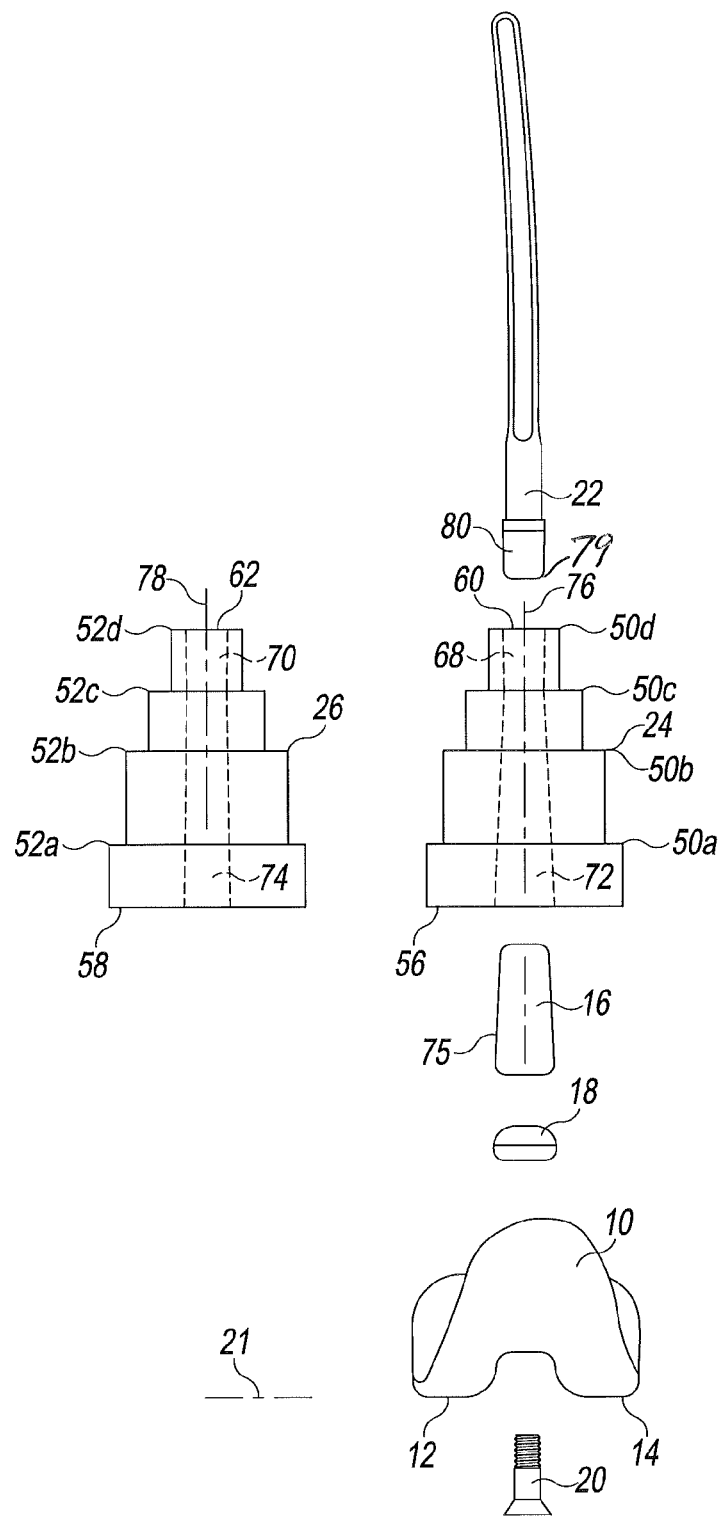
FIG. 1 is a view of the femoral components of a modular knee prosthesis system.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Terms representing anatomical references, such as anterior and posterior, proximal, distal, etcetera, may be used throughout the specification in reference to the orthopaedic implants described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
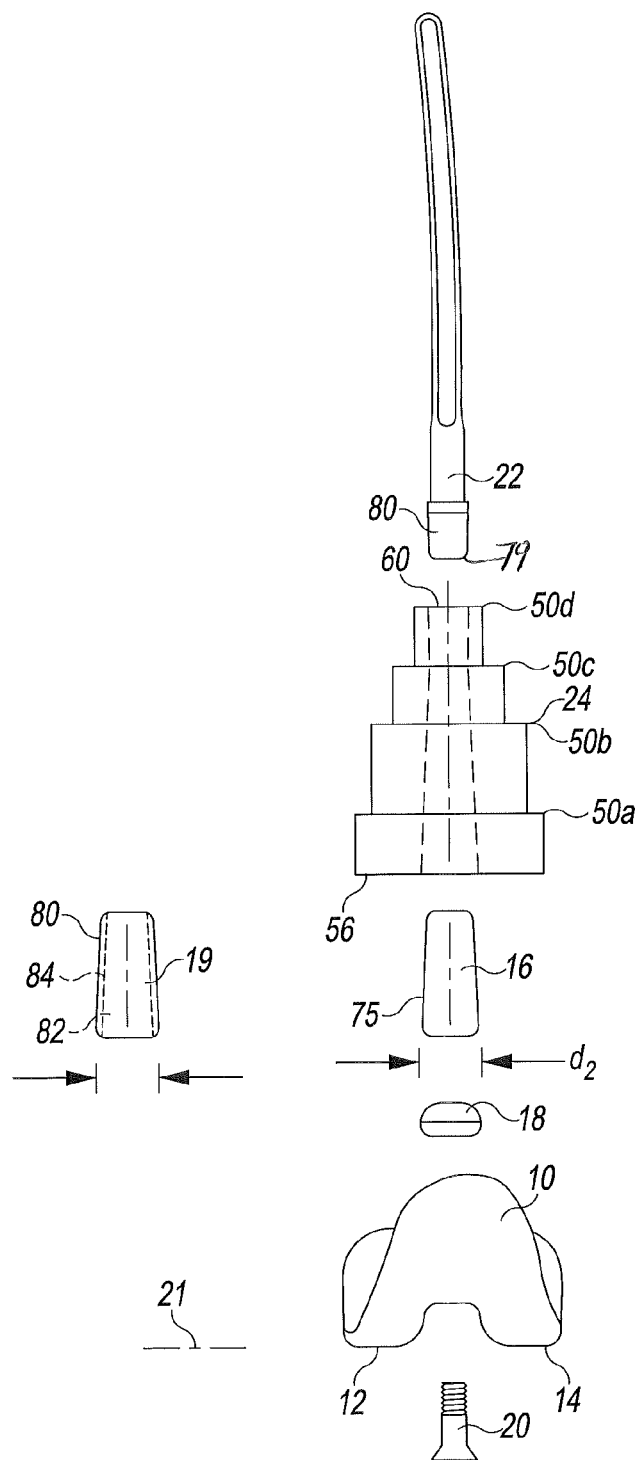
FIG. 2 is a view of an alternative embodiment of the femoral components of a modular knee prosthesis system.
Figure 3:
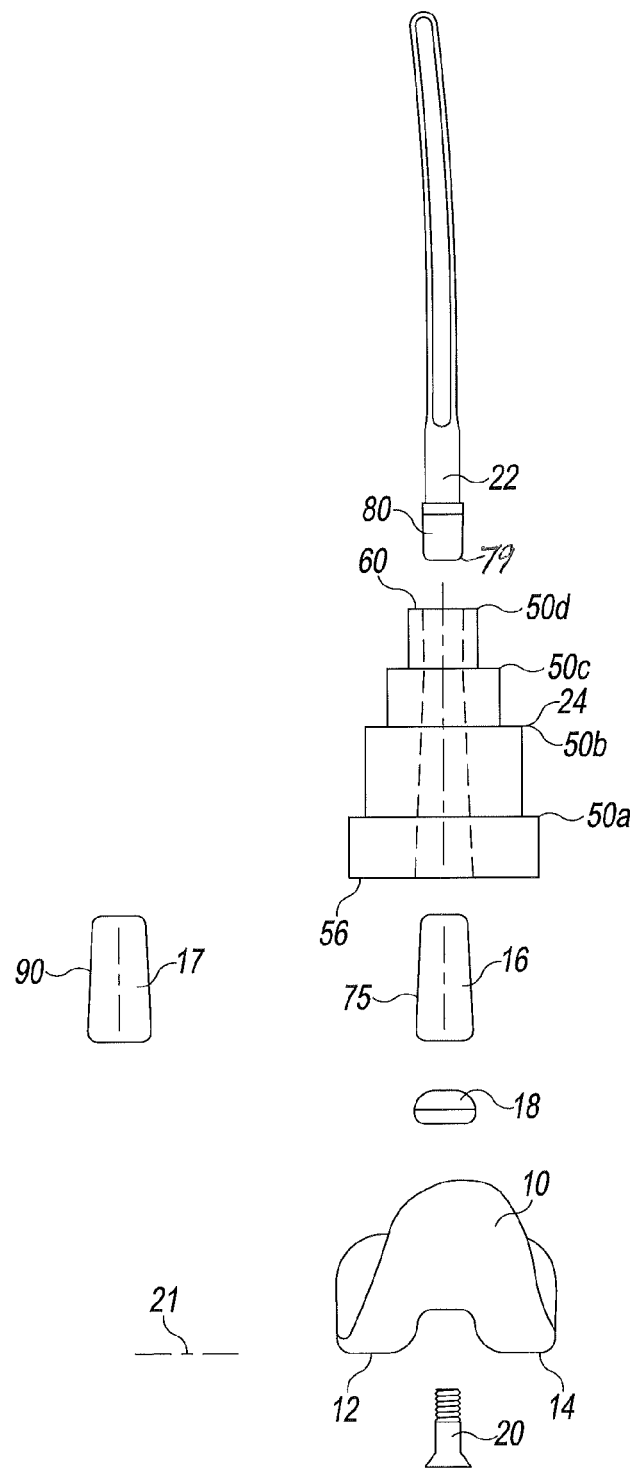
FIG. 3 is a view of another alternative embodiment of the femoral components of a modular knee prosthesis system.

FIGS. 1-3 illustrate examples of three embodiments of the femoral components of modular knee prosthesis systems illustrating the principles of the present invention. In each embodiment illustrated in FIGS. 1-3, the femoral components of the system include a distal femoral component 10 with distal curved convex condylar surfaces 12, 14. The illustrated distal femoral components are posterior stabilized components. Each embodiment includes at least one femoral stem 16, along with a collar 18 for placement between the stem 16 and the distal femoral component 10 and a bolt 20 so that the stem 16 and collar 18 may be selectively mounted on the distal femoral component. Each stem 16 has a frusto-conical outer surface that is smooth and tapers from a maximum outer diameter at the distal end to smaller outer diameters at positions proximal to the distal end. Stem extensions 22 are also provided. All of the above components may be standard parts of the P.F.C. SIGMA.® Knee System available from DePuy Synthes Sales, Inc. Each stem 16 in the illustrated embodiments is an adapter with features like those illustrated in U.S. Pat. Pub. No. 2006/0030945, entitled "Modular Orthopaedic Implant System with Multi-Use Stems." The stems 16 may also have features like those illustrated in U.S. Pat. No. 6,171,342, entitled "Medical Fastening System," U.S. Pat. No. 5,824,097, entitled "Medical Fastening System," U.S. Pat. No. 5,782,921, entitled "Modular Knee Prosthesis." Also as described in U.S. Pat. Pub. No. 2006/0030945, the stem extension may have features other than those illustrated in FIG. 1. It should be understood that these components are described for purposes of illustration only; the present invention is not limited to any particular type of distal femoral component or stem or any other particular component unless expressly called out in the claims. For example, in some embodiments, the femoral component 10 may have an integral stem 16 instead of the illustrated stem adapter 16, collar 18 and bolt 20.

In the embodiment of FIG. 1, the femoral components of the system include two types of metaphyseal members or sleeves 24, 26. As described in more detail below, the exterior surfaces of the two types of metaphyseal sleeves 24, 26 may be substantially the same, the sleeves 24, 26 differing in the sizes of the interior channels that mount on the stem 16 of the femoral component 10. It should be understood that multiple sizes of distal femoral components 10, metaphyseal sleeves 24, 26 and stem extensions 22 would typically be included in the modular knee prosthesis system.

In the embodiment of FIG. 2, the femoral components of the system include a shim 19 with a single type of stem adapter 16 (or integral distal femoral component and stem) and a single type of metaphyseal sleeve. As described in more detail below, the shim 19 is designed to fit over the exterior surface of the stem 16 to effectively increase the stem outer diameter that is received within the metaphyseal sleeve 24. Alternatively, for distal femoral components 10 with integral stems instead of adapters, the shim 19 would be designed to fit over the exterior surface of the stem of the distal femoral component 10.

In the embodiment of FIG. 3, the femoral components of the system include two types of stem adapters 16, 17 and a single type of metaphyseal sleeve 24. As described in more detail below, the stem adapters 16, 17 are similar, but differ in outer diameter. Alternatively, for distal femoral components 10 with integral stems instead of stem adapters, different femoral components may be provided with stems having different outer diameters.

With all three embodiments illustrated in FIGS. 1-3, the surgeon is provided with the opportunity to distalize the distal femoral component 10, to selectively increase the distance between the distal articulation surface plane 21 of the distal femoral component and the distal ends 56, 58 of the metaphyseal sleeves 24, 26.

Figure 4:
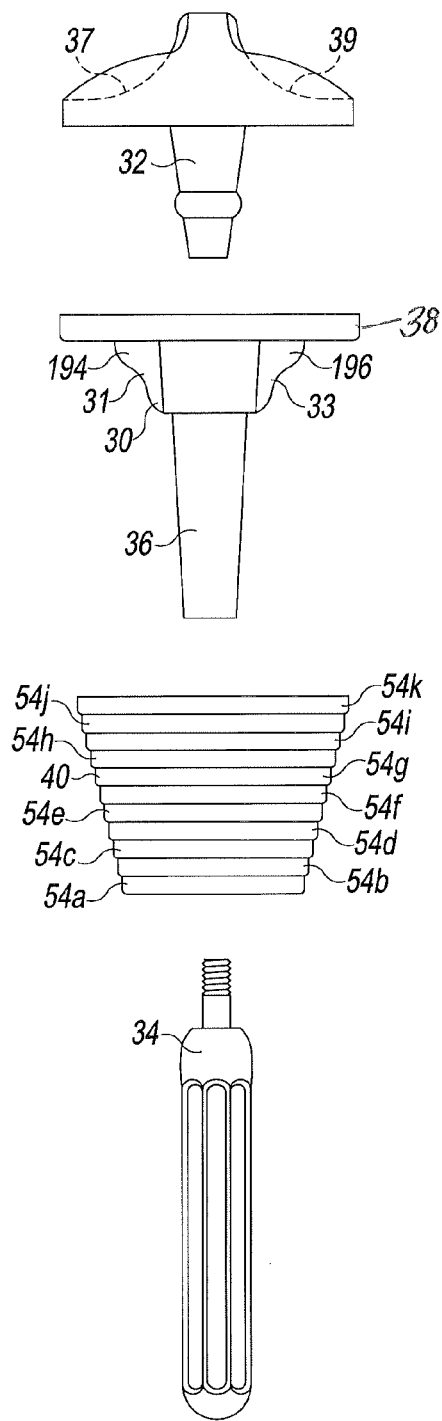
FIG. 4 is a view of the tibial components of a modular knee prosthesis system.

As illustrated in FIG. 4, on the tibial side, the kit includes a tibial tray component 30, a tibial bearing insert 32 and a stem extension 34. The illustrated tibial tray component 30 is a commercial MBT Revision tibial tray, available from DePuy Synthes Sales, Inc. The tray component 30 has an integral stem portion 36 with a bore (not shown) with internal threads to which the stem extension 34 may be attached. The outer surface of the stem portion 36 has a smooth finish, tapers away from the joint motion surface and is connected to the inferior surface of the tibial tray component 30 through keels 31, 33. The stem portion 36 extends distally from a platform 38, which has a proximal surface on which the tibial bearing insert 32 rests. The tibial components may also include one or more types or sizes of metaphyseal sleeves, such as sleeve 40 that has a tapered bore (not shown) sized and shaped to frictionally lock with the tapered stem portion 36 of the tibial tray component 30. It should be understood that these tibial components are described for purposes of illustration only; the present invention is not limited to any particular type of tibial component or stem or any other particular component unless expressly called out in the claims. For example, the tibial component may comprise a unitary, all-polymer component or a fixed bearing system, such as those disclosed in U.S. Pat. No. 7,628,818 and U.S. Pat. No. 8,128,703 (which are incorporated by reference herein in their entireties).

The juncture of the curved convex condyles 12, 14 of the distal femoral component 10 and the curved concave condylar surfaces of the tibial bearing insert 32 (the curved concave condylar surfaces of the tibial bearing insert being shown in FIG. 4 in phantom at 37, 39) define the articulation of the femoral and tibial components as the knee flexes and extends. When the patient's leg is in extension, the contact between the curved convex condyles 12, 14 and concave condylar surfaces 37, 39 corresponds with a distal joint line. As the knee is flexed from full extension, the distal femoral component 10 and tibial bearing insert 32 move with respect to each other so that the joint line at full flexion (when the posterior surfaces of the femoral condyles contact the bearing surface) may vary somewhat from the distal joint line. The plane of the joint line, tangent to the point of contact of the condylar surfaces of the distal femoral component on the tibial insert, is shown at 21 in FIGS. 1-3 and 9 and at 21A in FIG. 10.

The metaphyseal sleeves 24, 26, 40 are designed for use in a bone wherein the condition of the bone requires additional support or fixation in the metaphysis of the bone. All of these sleeves 24, 26, 40 have outer surfaces that have a plurality of adjacent steps or terraces, shown at 50a, 50b, 50c and 50d for the sleeve 24, at 52a, 52b, 52c and 52d for the sleeve 26 and at 54a, 54b, 54c, 54d, 54e, 54F, 54g, 54h, 54i, 54j and 54k for the sleeve 40. For the femoral sleeves, the outer surfaces taper proximally: the steps 50a, 52a at the distal ends 56, 58 have the largest anterior-posterior and medial-lateral dimensions and the steps 50d, 52d at the proximal ends 60, 62 have the smallest anterior-posterior and medial-lateral dimensions; the intermediate steps 50b, 50c, 52b, 52c gradually become smaller from the distal ends 56, 58 toward the proximal ends 60, 62. For the tibial sleeve 40, the outer surface tapers distally: the most distal step 54a has the smallest anterior-posterior and medial-lateral dimensions and the most proximal step 54k has the largest anterior-posterior and medial-lateral dimensions; the intermediate steps 54b, 54c, 54d, 54e, 54f, 54g, 54h, 54i and 54j gradually become smaller from the proximal end toward the distal end.

It should be understood that the number and size of the steps 50a, 50b, 50c 50d, 52a, 52b, 52c 52d, 54a, 54b, 54c, 54d, 54e, 54f, 54g, 54h, 54i, 54j and 54k may vary from the number and size of steps in the illustrated embodiments. For example, the outer surfaces of the metaphyseal sleeves 24, 26, 40 may have steps and be shaped like standard commercially available metaphyseal sleeves sold by DePuy Synthes Sales, Inc., and may be configured like the sleeves disclosed in the prior art, such as, for example, U.S. Pat. No. 7,799,085. It should also be understood that the shapes of the individual steps may be like those disclosed in the prior art, including for example, U.S. Pat. No. 7,799,085. The outer surfaces of the sleeves 24, 26, 40 may also be porous coated to promote bone ingrowth, as disclosed in the prior art.

Each of the illustrated femoral sleeves 24, 26 has an interior surface 64, 66 defining a proximal bore 68, 70 and a distal bore 72, 74. The proximal and distal bores 68, 70, 72, 74 in each femoral sleeve may be connected and aligned along central longitudinal axes 76, 78 of the bores.

The proximal bores 68, 70 of each femoral sleeve are sized and shaped to receive a distal end 79 of a stem extension 22. Accordingly, for a stem extension having a Morse taper post at its distal end, the proximal bore would comprise a Morse taper bore sized and shaped to receive and frictionally lock with the Morse taper post. Alternatively, for a stem extension having a threaded distal end, the proximal bore may be threaded to receive and lock to the threaded distal end of the stem extension. An adapter to allow for use of different types of stem extensions may also be used, as disclosed in U.S. Pat. No. 7,799,085.

The distal bores 72, 74 of the femoral metaphyseal sleeves 24, 26 are frusto-conical Morse taper bores, tapering from the distal ends 56, 58 of the sleeves 24, 26 toward the proximal ends 60, 62 of the sleeves 24, 26. These distal bores 72, 74 are sized, shaped and finished to be mountable on the stem or adapter 16 of the distal femoral component 10 and to create a frictional lock between the stem of the distal femoral component and the metaphyseal sleeve, the stem or adapter 16 defining a Morse taper post.

As used herein, "Morse taper" refers to locking tapers between mating components. Generally, Morse taper posts and bores have frusto-conical shapes, substantially the same taper angle and have complementary outer and inner diameters at some point along their length to allow for tight frictional engagement between the posts and the walls defining the bores. Standard taper angles and standard surface finishes for such locking tapers may be used in the present invention.

Figure 5:
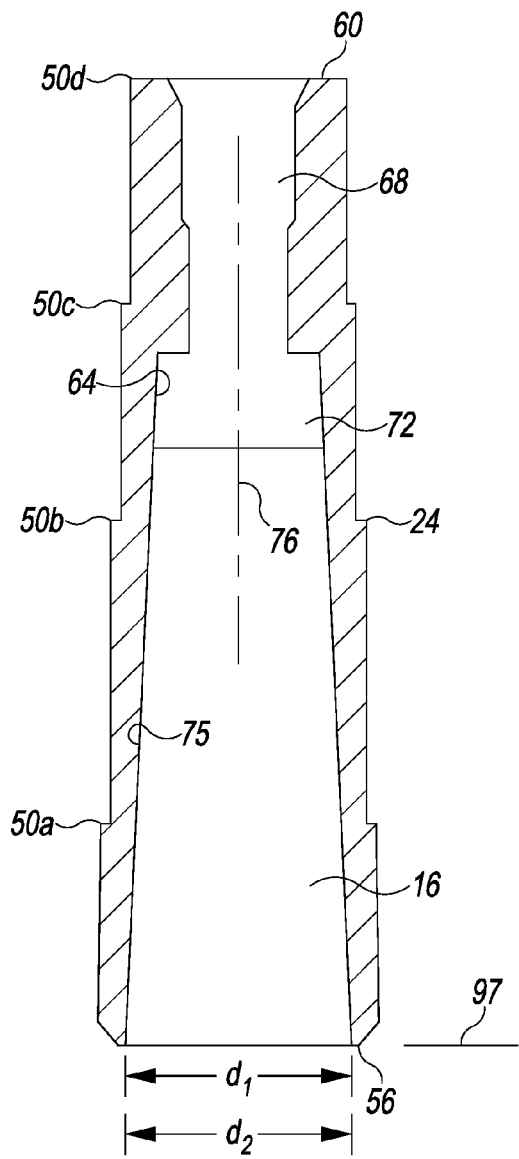
FIG. 5 is a cross-sectional view of one of the metaphyseal sleeves of the modular knee prosthesis system of FIG. 1, shown mounted on the stem of FIG. 1 (the stem shown in side view)

In the embodiment of FIG. 1, the distal bore 72 of the first type of sleeve 24 has a maximum inner diameter shown at $d_1$ in FIG. 5. This maximum inner diameter is at the distal end of the distal bore 72 and substantially corresponds with the maximum outer diameter of the tapered frusto-conical outer surface 75 of the stem or adapter 16 of the distal femoral component 10, shown at $d_2$ in FIGS. 5-7 at the distal end of each stem or adapter 16. Both the distal bore 72 of the sleeve 24 and the tapered frusto-conical outer surface 75 of the stem or adapter 16 taper in the proximal direction at substantially the same taper angle so that relative axial movement of the sleeve 24 and stem or adapter 16 locks the two together in the position shown in FIG. 5 when the interior surface 64 of the sleeve 24 engages and frictionally locks with the tapered frusto-conical outer surface 75 of the stem or adapter 16. Similarly, the distal bore 74 of the sleeve 26 and the tapered frusto-conical outer surface 75 of the stem or adapter 16 taper in the proximal direction at substantially the same taper angle so that relative axial movement of the sleeve 26 and stem or adapter 16 locks the two together in the position shown in FIG. 6 when the interior surface 66 of the sleeve 26 engages and frictionally locks with the outer surface 75 of the stem or adapter 16.

Figure 6:
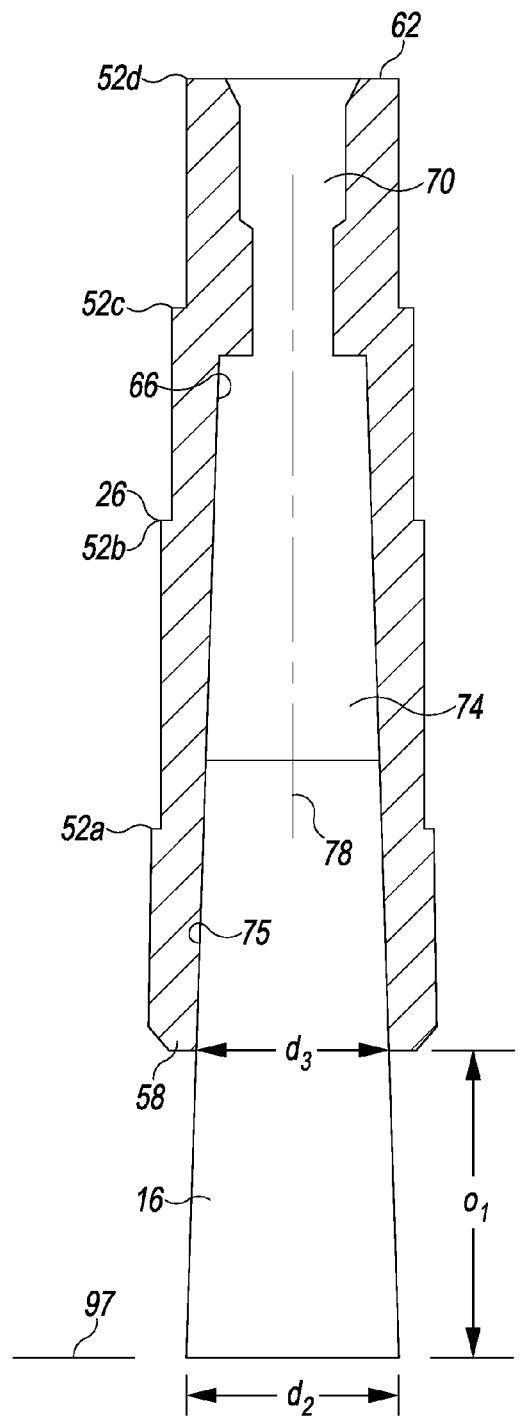
FIG. 6 is a cross-sectional view of the other metaphyseal sleeve of the modular knee prosthesis system of FIG. 1, shown mounted on the stem of FIG. 1 (the stem shown in side view)

As shown in FIGS. 5-6, the distal bore 74 of the sleeve 26 has a smaller maximum inner diameter $d_3$ than the maximum inner diameter $d_1$ of the distal bore 72 of the sleeve 24. This maximum inner diameter $d_3$ of the distal bore 74 is also less than the maximum outer diameter of the stem or adapter 16 of the distal femoral component 10 so that when the sleeve 26 is mounted and frictionally-locked to the stem or adapter 16, a portion of the stem or adapter 16 is exposed beyond the distal end of the distal bore 74. The overall axial length of the construct is thus increased, thereby distalizing the femoral component 10 when implanted. The distance between $d_2$ and $d_3$ is the axial or distal offset provided when using the second sleeve 26, shown at $o_1$ in FIG. 6.

In this embodiment, the overall axial lengths and the sizes and shapes of the outer surfaces of the two sleeves 24, 26 are the same so that preparation of the distal femur to receive either of the two sleeves 24, 26 is the same. No additional bone must be removed to distalize the femoral component 10.

In the embodiment of FIG. 2, the shim 19 comprises a frusto-conical tube, with a tapered outer surface 80 and a tapered through-bore 82 defined by an inner wall 84. As shown in FIG. 7, the outer surface 80 of the shim 19 is sized and shaped to be received within and frictionally lock with the metaphyseal sleeve 24. The tapered through-bore 82 and inner wall 84 are sized and shaped to receive and frictionally lock with the stem or adapter 16. Thus, the outer surface 80 of the shim 19 defines a Morse taper post and the tapered through-bore 82 defines a Morse taper bore.

As shown in FIG. 7, the through-bore 82 of the shim 19 has a maximum inner diameter at its distal end, shown at $d_4$. The outer surface 80 of the shim 19 has a maximum outer diameter shown at $d_5$ in FIG. 7. In this embodiment, the maximum outer diameter $d_5$ of the shim 19 is substantially the same as the maximum outer diameter $d_2$ of the stem or adapter 16 and the maximum inner diameter $d_4$ of the through-bore 82 is less than the maximum outer diameter $d_2$ of the stem or adapter 16 and less than the maximum inner diameter $d_1$ of the first sleeve 24. The outer surface 80 of the shim 19 has smaller outer diameters at more proximal positions and the through-bore 82 has smaller inner diameters at more proximal positions.

The shim 19 and the sleeve 24 may be assembled by placing the proximal end of the shim in the distal end of the sleeve distal bore 72 and moving the components 19, 24 axially until the outer surface 80 of the shim 19 and interior surface 64 of the sleeve engage and frictionally lock together as a Morse taper lock. This assembly may then be mounted on the stem or adapter 16 by placing the proximal end of the stem or adapter 16 into the distal end of the through-bore 82 of the shim/sleeve assembly and moving the components axially until the tapered interior surface 84 of the shim 19 engages and frictionally locks with the matching tapered frusto-conical outer surface 75 of the stem or adapter 16. Alternatively, the shim 19 may be mounted on the stem or adapter 16 and then the sleeve mounted on the assembly of the shim and stem or adapter.

Since the maximum inner diameter $d_4$ of the shim/sleeve assembly is less than the maximum outer diameter $d_2$ of the stem or adapter 16, the shim/sleeve assembly and the stem or adapter 16 engage and lock together with a portion of the stem or adapter 16 exposed beyond the distal end of the distal bore 82 of the shim 19. The overall axial length of the construct is thus increased, thereby distalizing the femoral component 10 when implanted. The distance between $d_2$ and $d_4$ is the axial or distal offset provided when using the shim/sleeve assembly, shown at $o_2$ in FIG. 7. Stated another way, since the maximum outer diameter of the stem or adapter and shim assembly is greater than the maximum inner diameter of the sleeve, the shim/stem assembly engages and locks together with the sleeve such that a portion of the shim/stem assembly is exposed beyond the distal end of the distal bore of the sleeve and the overall axial length of the construct is increased, thereby distalizing the femoral component 10 when implanted and providing the offset $o_2$.

As in the first embodiment, the overall axial length and the size and shape of the outer surface of the first sleeve 24 remains the same in this embodiment, both without the shim as shown in FIG. 5 and with the shim 19 as shown in FIG. 7. Thus, as in the embodiment of FIG. 1, the femoral component 10 may be distalized while using the same bone cavity to receive the sleeve.

In the embodiment of FIG. 3, the second stem adapter 17 has a frusto-conical tapered outer surface 90 set at the same taper angle as the first stem adapter 16, and has substantially the same length as the first stem adapter 16, but has a greater maximum outer diameter $d_6$ than the first stem adapter 16. As shown in FIG. 8, the outer surface 90 tapers to a position where its outer diameter $d_7$ is the same as the maximum inner diameter $d_1$ of the distal bore 72 of the first type of sleeve 24 and the same as the maximum outer diameter $d_2$ of the first stem adapter 16. The outer diameter $d_7$ is spaced axially in a proximal direction from the distal end of the second stem adapter 17.

In the embodiment of FIG. 3, the surgeon has the option of assembling the distal femoral component with either stem adapter 16, 17. If the first stem adapter 16 is selected, when the sleeve 24 is mounted and frictionally-locked to the assembly the axial position of the sleeve relative to the stem 16 would be as shown in FIG. 5. If the second stem adapter 17 is selected, when the first sleeve 24 is mounted and frictionally-locked to the assembly the axial position of the sleeve relative to the stem 17 would be as shown in FIG. 8.

Since the maximum outer diameter $d_6$ of the second stem adapter 17 is greater than the maximum outer diameter $d_2$ of the first stem adapter 16, the sleeve 24 and the stem adapter 17 engage and lock together with a portion of the stem adapter 17 exposed beyond the distal end of the distal bore 72 of the sleeve 24 and the overall axial length of the construct is increased, thereby distalizing the femoral component 10 when implanted. The distance between $d_6$ and $d_7$ is the axial or distal offset provided when using the second stem adapter 17, shown at $o_3$ in FIG. 8.

As shown in FIGS. 5-7, the central longitudinal axes 76, 78 of the tapered bores 72, 74 intersect planes at the distal ends of the stems 16, 17. These planes are shown in FIGS. 5-7 at 97. With the standard metaphyseal member 24 and stem 16 shown in FIG. 5, the distal end of the bore 72 may lie in plane 97. As shown in FIG. 6, the distal end of the bore 74 is spaced from the plane 97 by the offset distance $o_1$. As shown in FIG. 7, the distal end of the bore 72 is spaced from the plane 97 by the offset distance $o_2$. As shown in FIG. 8, the distal end of the bore 72 is spaced from the plane 97 by the offset distance $o_3$.

Figure 11:
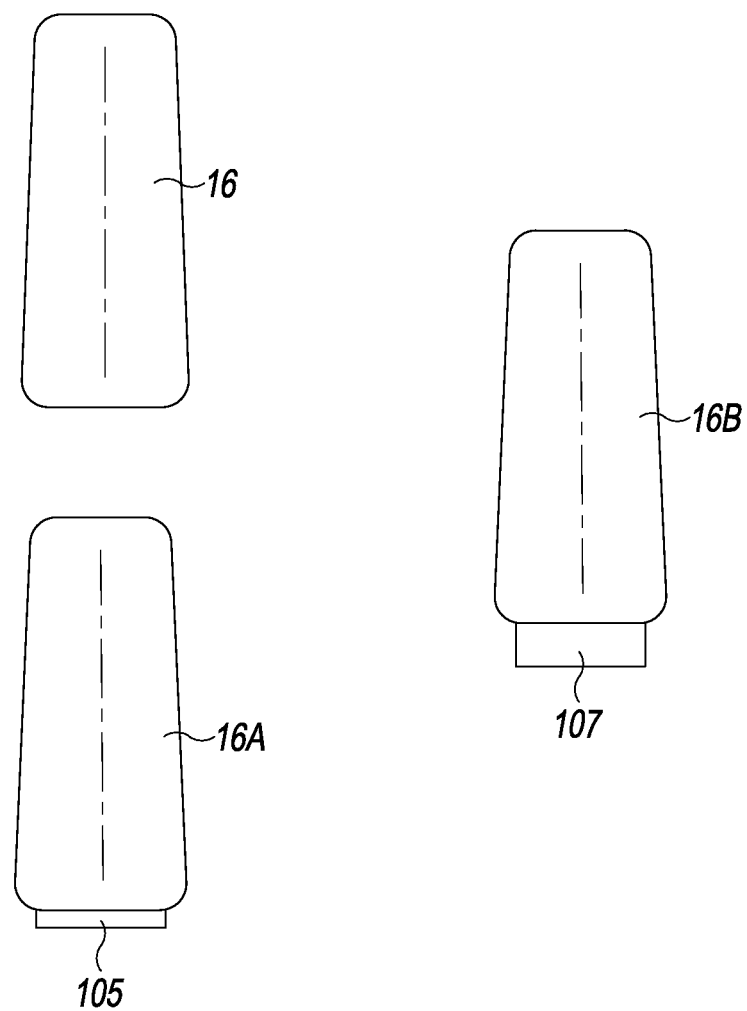
FIG. 11 is a side view of an alternative set of stem adapters that may be used with the modular knee prosthesis system of FIG. 3.

It should be understood that other options may be provided for a system including multiple stem adapters to selectively offset the distal femoral component. For example, a standard stem adapter defining a Morse taper post could be provided, along with additional stem adapters having the same Morse taper post at the proximal ends but with greater overall lengths. FIG. 11 illustrates such an alternative, where the standard stem adapter is shown at 16 and the additional stem adapters are illustrated at 16A and 16B. Stem adapters 16A and 16B include distal extensions 105, 107 that extend the overall axial lengths of the stem adapters by defined increments, such as by 5 mm increments. Thus, the surgeon may adjust the distal offset to meet the needs of the individual patient.

It will be appreciated that the options available to the surgeon may be increased by increasing the number of components in the system. For example, in the first embodiment, additional sleeves having the same exterior geometry and different diameters of Morse taper bores could be provided. In the second embodiment, additional shims 19 could be provided, each having a Morse taper bore of the same shape but with tapered outer surfaces having different outer diameters. In the third embodiment, additional stem adapters could be provided, each having a different maximum outer diameter.

Figure 9:
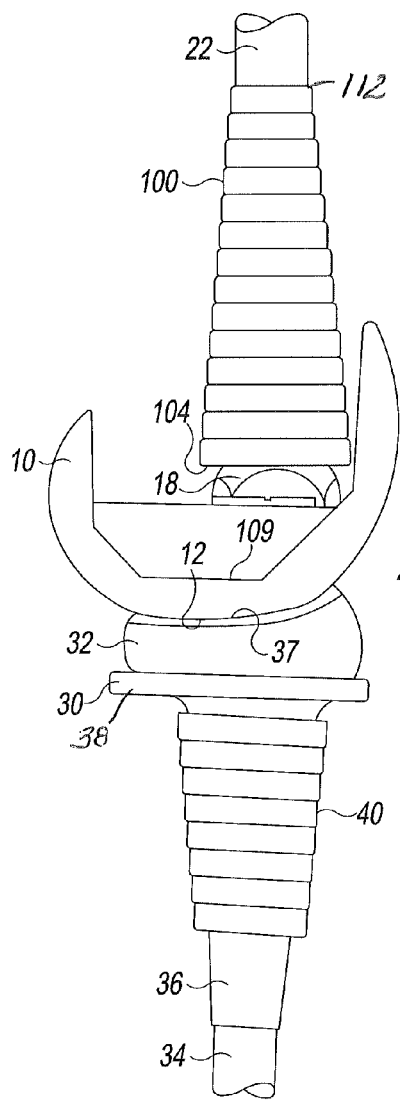
FIG. 9 is a side view of a modular knee prosthesis system using a standard femoral stem and femoral sleeve.
Figure 10:
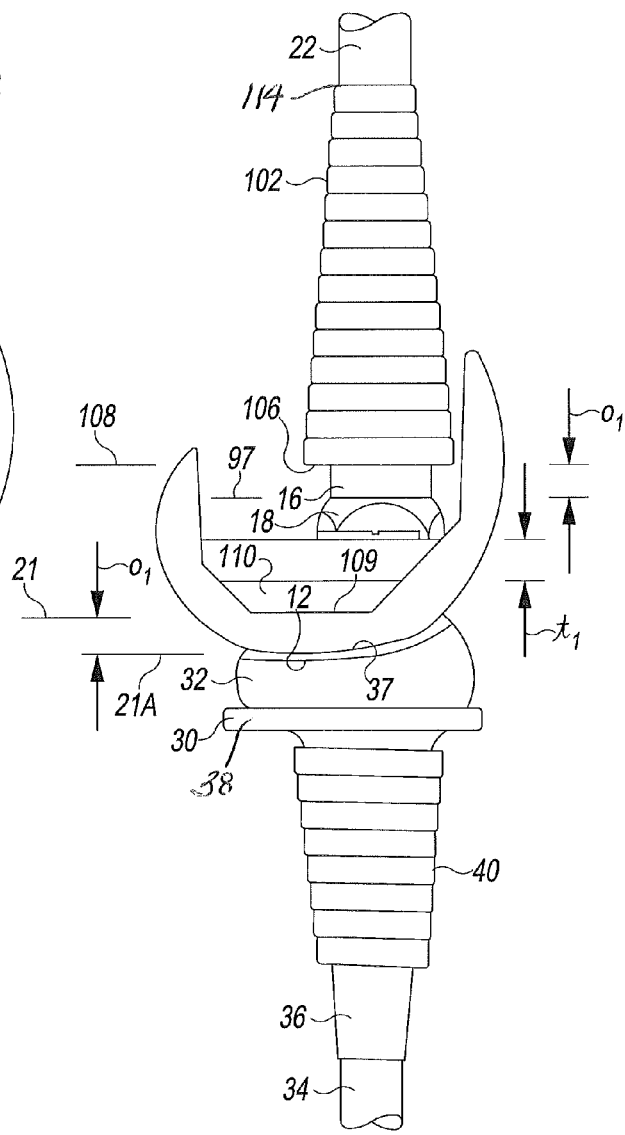
FIG. 10 is a side view of a modular knee prosthesis system similar to FIG. 9 but shown with a femoral sleeve having a more narrow bore, as in the embodiment of FIG. 1.

FIGS. 9 and 10 illustrate side views of assemblies of the femoral components similar to those illustrated in FIG. 1 in combination with the tibial components of FIG. 4. The femoral sleeves 100, 102 of FIGS. 9 and 10 are similar to the femoral components 24, 26 described above except that the exterior surfaces are more like those described in U.S. Pat. No. 7,799,085. However, like the sleeves 24, 26 of FIGS. 1 and 5-6, the sleeves 100, 102 of FIGS. 9 and 10 differ in that the maximum inner diameter of the Morse taper bore of the sleeve 102 of FIG. 10 is smaller than the maximum inner diameter of the Morse taper bore of the sleeve 100 of FIG. 9.

As can be seen from a comparison of FIGS. 9 and 10, the distal ends 104, 106 of the sleeves 100, 102 lie in the same plane 108, illustrating that the position of the sleeves 100, 102 with respect to the distal femur (not shown) is the same, when either of the sleeves 100, 102 is used. However, as can also be seen from a comparison of FIGS. 9 and 10, using the second sleeve 102 distalizes the joint line 21 to the position 21A by the offset distance $o_1$. As shown in FIG. 10, this offset distance $o_1$ also corresponds with the axial length of the portion of the stem or adapter 16 exposed distal to the distal end 106 of the sleeve 102. It will be appreciated that substantially the same results would be obtained using the embodiments of FIG. 2 or FIG. 3.

FIG. 10 illustrates the femoral components used in conjunction with a standard distal femoral augment 110, shown mounted on a distal bone-facing surface 109 of the distal femoral component. The distal femoral augment 110 has a thickness $t_1$ shown in FIG. 10; this thickness $t_1$ corresponds with the distal offset $o_1$ in the illustrated embodiment, although it should be understood that an implant system or kit may include multiple sizes of distal augments having varying thicknesses. The distal femoral augments may have standard features, such as those disclosed in U.S. Pat. No. 6,005,018 and U.S. Pat. No. 5,984,969.

FIGS. 9 and 10 also illustrate that the overall length of each femoral implant assembly can be selectively adjusted to meet patients' needs. In FIG. 9, the overall length of the femoral implant assembly from the proximal end 112 of the sleeve 100 to the joint line 21, shown at $l_1$, is less than the overall length of the femoral implant assembly shown in FIG. 10 at 12 (from the proximal end 114 of the sleeve 102 to the joint line 21A). The difference between $l_1$ and $l_2$ is the distal offset $o_1$.

As discussed above, it should be appreciated that a standard kit using the above-described embodiments may include multiple components to provide the surgeon with a variety of distal offset choices to meet the needs of the individual patient. For example, the kit could provide the surgeon with sufficient components to intraoperatively select distal offsets $o_1$ of 0, 5 mm or 10 mm, for example.

It should also be appreciated that the principles of the present invention may also be applied to the tibial components of the knee implant system, such as the tibial sleeve 40 shown in FIG. 4. Such a system could allow the surgeon to select components to provide a proximal offset to the tibial tray platform 38. For example, such a system could include shims for mounting on the tibial stem 36, metaphyseal sleeves with the same outer size and shape but different bores, or metaphyseal sleeves with the same anterior-posterior and medial-lateral dimensions but different axial lengths.

When using any of the illustrated embodiments, the surgeon may prepare the bone to receive an optimally-sized the sleeve using, for example, standard broaches. If the surgeon determines that the needs of the individual patient are best served by distalizing the joint line, the surgeon can use the metaphyseal sleeve members of any of the illustrated embodiments using the same opening in the bone created by broaching. Thus, the surgeon may use an optimally sized metaphyseal sleeve with a distal femoral component and optimize of the joint line without the need for additional broaching.

All of the components of the illustrated implant system may be made of standard materials, such as a standard polymer (UHMWPE, for example) for the tibial bearing insert 32 and standard metals, such as cobalt-chromium and titanium alloys, for the remaining components. To promote bone ingrowth, the sleeves 24, 26, 40, 100, 102, 120 may be porous coated, or could comprise titanium foam as disclosed in U.S. Pat. No. 8,382,849 ("Porous Titanium Tibial Sleeves and Their Use in Revision Knee Surgery") and U.S. Pat. Pub. No. 20100076565 ("Porous Titanium Femoral Sleeves and Their Use in Revision Knee Surgery"), both of which are incorporated by reference herein in their entireties.

Titanium foam sleeves as disclosed in those patent applications may incorporate the principles of the present invention by providing sleeves with adapters having different maximum internal diameters to define sleeve/adapter constructs like the metaphyseal members or sleeves 24, 26 shown in FIG. 1, with the same outer surface but different internal mounting bores. The principles of the present invention may also be applied to titanium foam sleeve/adapter constructs by including one or more shims (such as shim 19 of the embodiment of FIG. 2) in the system with internal bores having different maximum internal diameters.

An alternative system providing the option of distalizing the joint line is disclosed in the application for United States Patent filed concurrently herewith entitled "Modular Knee Prosthesis System with Multiple Lengths of Sleeves Sharing Common Geometry," (Ser. No. 61/703,404), filed by Thomas L. Bernasek, Lawrence S. Crossett, Brian D. Haas, George J. Haidukewych, Jay R. Lieberman, Benjamin J. Sordelet, Richard Spencer Jones, Timothy G. Vendrely and Stephanie M. Wainscott, which is incorporated by reference herein in its entirety.

It will be noted that alternative embodiments of each of the systems of the present disclosure may not include all of the features described yet still benefit from at least some of the advantages of such features. Those of ordinary skill in the art may readily devise their own implementations of a system that incorporates one or more of the features of the present disclosure and fall within the spirit and scope of the invention as defined by the appended claims.

We claim:
1. A modular knee prosthesis system comprising:
a distal femoral component having a distal bone-facing surface, a pair of spaced, curved distal condylar surfaces and a stem having an outer surface tapering from a distal end in the proximal direction, the outer surface of the stem having a maximum outer diameter at the distal end and a smaller outer diameter at a second position proximal to the distal end;
a first metaphyseal member having an outer surface that tapers in a proximal direction and an inner surface defining a tapered bore sized and shaped to be mountable on the stem of the distal femoral component and to create a frictional lock between the stem of the distal femoral component and the first metaphyseal member, the tapered bore having a maximum inner diameter at a distal end, the maximum inner diameter corresponding with the maximum outer diameter of the stem of the distal femoral component;
the tapered bore of the first metaphyseal member having a central longitudinal axis that intersects a plane at the distal end of the stem of the distal femoral component when the first metaphyseal member is mounted on the stem of the distal femoral component, the distal end of the tapered bore and the plane being at a first distance;

a second metaphyseal member having an outer surface that tapers in a proximal direction and an inner surface defining a tapered bore sized and shaped to be mountable on the stem of the distal femoral component and to create a frictional lock between the stem of the distal femoral component and the second metaphyseal member, the tapered bore having a maximum inner diameter at a distal end, the maximum inner diameter corresponding with the outer diameter of the stem of the distal femoral component at the second position so that the first metaphyseal member and the second metaphyseal member are mountable on the stem of the distal femoral component to create frictional locks at different positions in the proximal-distal direction on the stem of the distal femoral component;

the tapered bore of the second metaphyseal member having a central longitudinal axis that intersects a plane at the distal end of the stem of the distal femoral component when the second metaphyseal member is mounted on the stem of the distal femoral component, the distal end of the tapered bore and the plane being at a second distance, the second distance being greater than the first distance; and a distal femoral augment having a thickness;

wherein the difference between the first distance and the second distance defines a distal offset of the distal femoral component and the thickness of the distal femoral augment is substantially the same as the distal offset provided by the second metaphyseal member.

2. The modular knee prosthesis system of claim 1 wherein the second metaphyseal member comprises an assembly of a sleeve and a first shim, wherein:

the sleeve has an outer surface that defines the outer surface of the second metaphyseal member and an inner surface defining a tapered bore sized and shaped to be mountable on the stem of the distal femoral component and to create a frictional lock between the stem of the distal femoral component and the first metaphyseal member, the tapered bore having a maximum inner diameter at a distal end and a smaller inner diameter at a second more proximal position, the size and shape of the tapered bore of the sleeve being substantially the same as the size and shape of the tapered bore of the first metaphyseal member; and the first shim comprises a tapered tube having an outer surface sized and shaped to be received within and frictionally lock with the tapered bore of the sleeve and an inner surface defining a tapered bore sized and shaped to be mountable on the stem of the distal femoral component and to create a frictional lock between the stem of the distal femoral component and the first shim, the tapered bore of the first shim having a maximum inner diameter at a distal end and a second inner diameter at a second more proximal position, the maximum inner diameter of the first shim defining the maximum inner diameter of the second metaphyseal member when the first shim and sleeve are assembled.

3. The modular knee prosthesis system of claim 2 wherein a distal portion of the stem is exposed when the sleeve and first shim are frictionally locked on the stem.

4. The modular knee prosthesis system of claim 2 wherein the outer surfaces of the first metaphyseal member and the sleeve have the same size and shape.

5. The modular knee prosthesis system of claim 1 further comprising a tibial member having an articulating surface to receive and articulate with the distal articulating surfaces of the distal femoral component, the contact between the articulating surfaces of the tibial member and the distal femoral component defining a joint line.

6. The modular knee prosthesis system of claim 5 wherein:

the tibial member and an assembly of the distal femoral component and the first metaphyseal member defines a first joint line and the tibial member and an assembly of the distal femoral component and the second metaphyseal member defines a second joint line; and the second joint line is more distal than the first joint line.

7. A modular knee prosthesis system comprising:

a distal femoral component having a pair of spaced, curved distal condylar surfaces;

a tibial member having an articulating surface to receive and articulate with the distal articulating surfaces of the distal femoral component, the contact between the articulating surfaces of the tibial member and the distal femoral component defining a joint line;

a first metaphyseal member having an outer surface that tapers in a proximal direction and an inner surface defining a bore tapering from a maximum inner diameter at a distal end to a smaller inner diameter at a second more proximal position;

a first stem adapter selectively mountable on the distal femoral component and having an outer surface tapering from a distal end in the proximal direction, the outer surface of the stem having a maximum outer diameter at a distal end and a smaller outer diameter at a second position proximal to the distal end; and a second stem adapter selectively mountable on the distal femoral component and having an outer surface tapering from a distal end in the proximal direction, the outer surface of the stem having a maximum outer diameter at a distal end and a smaller outer diameter at a second position proximal to the distal end;

wherein the maximum outer diameter of the second stem adapter is greater than the maximum outer diameter of the first stem adapter;

wherein the bore of the first metaphyseal member is sized and shaped to be mountable on the first stem adapter and to create a frictional lock between the first metaphyseal member and the first stem adapter;

wherein the bore of the first metaphyseal member is sized and shaped to be mountable on the second stem adapter and to create a frictional lock between the first metaphyseal member and the second stem adapter;

wherein when the first metaphyseal member and first stem adapter are locked together the distal end of the first stem adapter is in a proximal-distal position with respect to the bore of the first metaphyseal member;

wherein when the first metaphyseal member and second stem adapter are locked together the distal end of the second stem adapter is in a proximal-distal position with respect to the bore of the first metaphyseal member;

wherein the locked proximal-distal position of the first stem adapter is more proximal than the locked proximal-distal position of the second stem adapter with respect to the first metaphyseal member;

wherein the tibial member and an assembly of the femoral component, the first metaphyseal member and the first stem adapter define a first joint line at the contact between the articulating surfaces of the tibial member and the distal femoral component;

wherein the tibial member and an assembly of the femoral component, the first metaphyseal member and the second stem adapter define a second joint line at the contact between the articulating surfaces of the tibial member and the distal femoral component;

wherein the second joint line is more distal than the first joint line;

wherein the difference between the first proximal-distal position of the distal femoral component and the second proximal-distal position of the distal femoral component corresponds with a distal offset of the distal femoral component;

wherein the distal femoral component has a distal bone-facing surface; and wherein the system further comprises a distal femoral augment having a thickness, the thickness of the distal femoral augment being substantially the same as the distal offset of the distal femoral component.

* * * * *